United States Patent [19]

Schrock et al.

[11] Patent Number: 4,864,010

[45] Date of Patent: Sep. 5, 1989

[54] MONOMERS, OLIGOMERS, AND POLYMERS OF BISCYCLOBUTARENES BRIDGED BY AT LEAST ONE BENZOXAZOLE LINKAGE

[75] Inventors: Alan K. Schrock, Lake Jackson, Tex.; William J. Harris; Norman L. Madison, both of Midland, Mich.

[73] Assignee: The Dow Chemical Company, Midland, Mich.

[21] Appl. No.: 205,141

[22] Filed: Jun. 9, 1988

[51] Int. Cl.$^4$ .................. C08F 38/00; C08F 132/08
[52] U.S. Cl. .................. 528/185; 528/176; 528/183; 548/217; 548/577
[58] Field of Search .................. 528/176, 183, 185; 548/217, 577

[56] References Cited

U.S. PATENT DOCUMENTS

| | | | |
|---|---|---|---|
| 4,533,693 | 8/1985 | Wolfe et al. | 524/417 |
| 4,540,763 | 9/1985 | Kirchhoff | 526/281 |
| 4,578,432 | 3/1986 | Tsai et al. | 528/183 |
| 4,675,370 | 6/1987 | Tan et al. | 548/224 |
| 4,687,823 | 8/1987 | Kirchhoff et al. | 526/284 |
| 4,692,445 | 9/1987 | Kuhla et al. | 548/336 |

OTHER PUBLICATIONS

Denny et al., *Polymer Preprints*, vol. 29, No. 1, pp. 194–195 (Jun. 1988), entitled, "High Temperature Bisbenzocyclobutene (BCB) Terminated Resin Properties".
U.S. Ser. No. 883,240 to Kirchhoff dated Jul. 1986.
U.S. Ser. No. 132,734 to Schrock dated Dec. 1986.

*Primary Examiner*—Harold D. Anderson
*Assistant Examiner*—T. Mason
*Attorney, Agent, or Firm*—Matthew S. Goodwin

[57] ABSTRACT

A biscyclobutarene monomer is prepared comprising two cyclobutarene moieties bridged by a divalent radical having at least one benzoxazole linkage. A reactive biscyclobutarene oligomer is also prepared by reacting a cyclobutarene-carboxylic acid, a diaminodihydroxyarene, and either an aromatic diacid or an aromatic diacid chloride. The monomers and reactive oligomers can be polymerized to form polymers exhibiting outstanding thermooxidative stability at high temperatures for prolonged time periods.

20 Claims, 4 Drawing Sheets

MONOMERS, OLIGOMERS, AND POLYMERS OF BISCYCLOBUTARENES BRIDGED BY AT LEAST ONE BENZOXAZOLE LINKAGE

The U.S. Government has a paid-up license in this invention and the right in limited circumstances to require the patent owner to license others on reasonable terms as provided for by the terms of Contract No. F33615-85-C-5092 awarded by Wright-Patterson Air Force Base.

BACKGROUND OF THE INVENTION

This invention relates to monomers and oligomers of biscyclobutarenes and polymers derived therefrom. More specifically, it relates to monomers, oligomers, and polymers of biscyclobutarenes that are bridged by at least one benzoxazole linkage.

Polymers derived from biscyclobutarene monomers are disclosed in U.S. Pat. No. 4,540,763. The polymers are prepared by subjecting biscyclobutarene monomers to temperatures sufficient for polymerization. The polymers exhibit excellent thermal stability at high temperatures, good chemical resistance to most industrial solvents, good physical and mechanical properties, and low sensitivity to water. The polymers are useful for preparing composites, coatings and films; and as adhesives.

Although the polymers of U.S. Pat. No. 4,540,763 exhibit excellent thermal stability at high temperatures, numerous applications in high performance industries, such as the aerospace industry, require polymers for advanced composites that not only exhibit high temperature thermal stability but also exhibit high temperature thermal stability in air for prolonged time periods. Unfortunately, many of the polymers of U.S. Pat. No. 4,540,736 do not exhibit the long term thermooxidative stability required for high performance applications. The polyvalent organic and inorganic bridging groups of the biscyclobutarenes are susceptible to oxidation reactions when subjected to elevated temperatures for extended times. Particularly susceptible are aliphatic bridging groups.

In view of the deficiencies of the prior art, it would be desirable to prepare polymers derived from biscyclobutarene monomers and oligomers that exhibit outstanding thermooxidative stability for prolonged time periods.

SUMMARY OF THE INVENTION

In one aspect, the invention is a biscyclobutarene monomer and a biscyclobutarene oligomer derived therefrom. The biscyclobutarene monomer comprises two cyclobutarene moieties bridged by a divalent radical having at least one benzoxazole linkage. The biscyclobutarene oligomer comprises the reaction product of a cyclobutarene-carboxylic acid, a diaminodihydroxyarene, and either an aromatic diacid or an aromatic diacid chloride.

In another aspect, the invention comprises a process for preparing a polymer from the biscyclobutarene monomer or the biscyclobutarene oligomer of this invention. The process comprises the step of subjecting the monomer or oligomer to ring scission polymerization conditions.

The polymers derived from the biscyclobutarene monomers and the biscyclobutarene oligomers exhibit excellent thermooxidative stability at high temperatures for prolonged time periods. The benzoxazole linkage of the divalent radical contributes to the thermooxidative stability of the bridging member, and therefore the thermooxidative stability of the polymer is enhanced. The polymers are useful as matrix resins for advanced composites and as high performance adhesives for bonding substrates. They are also useful for any other application requiring service in a harsh environment.

DETAILED DESCRIPTION OF THE INVENTION

Figure 1:
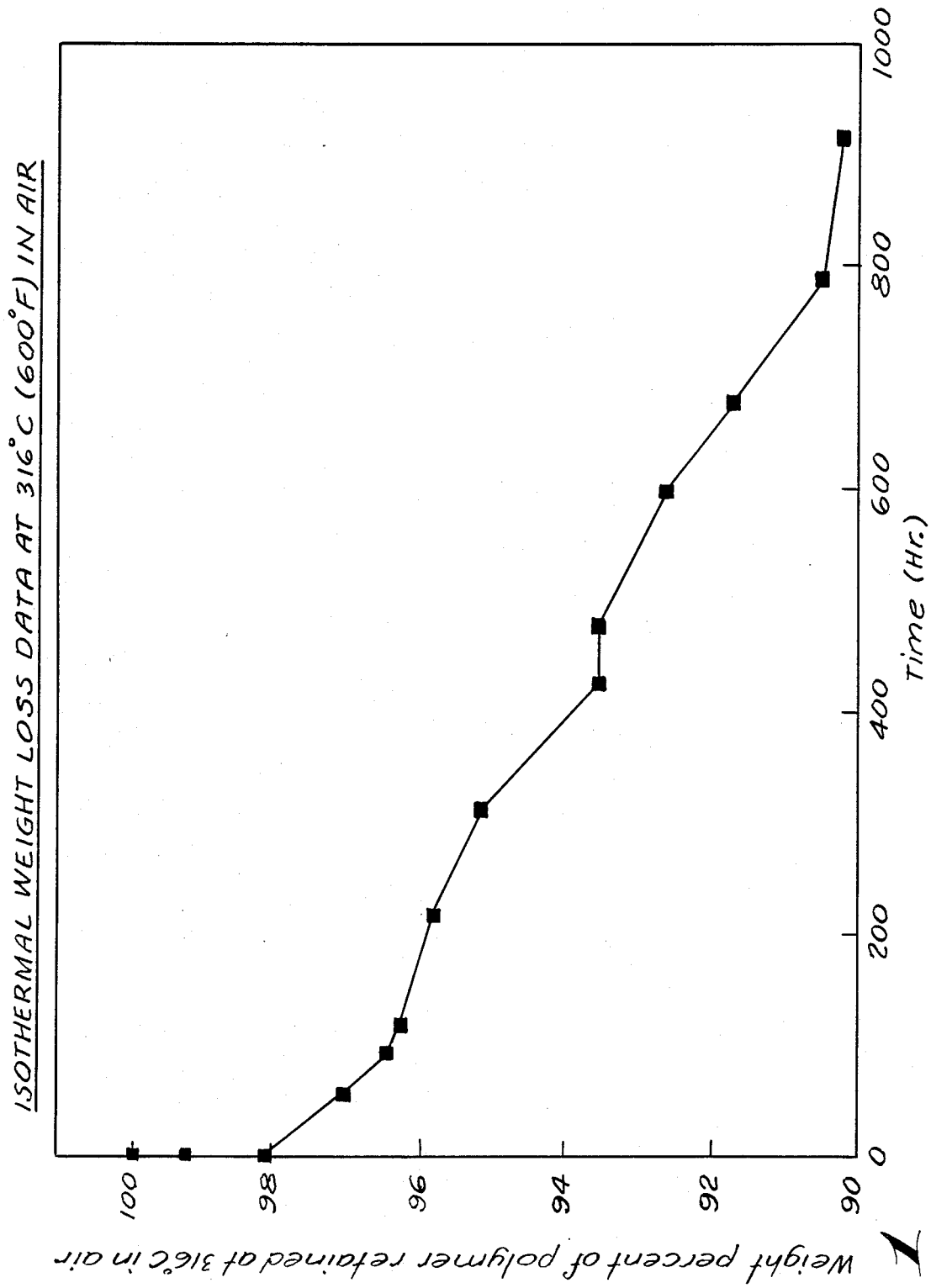
FIGS. 1-4 are graphs of the thermooxidative stability of polymers derived from preferred oligomers of this invention.

For purposes of describing this invention, a cyclobutarene is a substituted or unsubstituted aromatic compound to which is fused one or more cyclobutane rings or one or more substituted cyclobutane rings. The aromatic ring of the cyclobutarene can be substituted with nitro, chloro, bromo, or any other group that will not adversely affect the thermooxidative stability of the polymers derived from the monomers of this invention. Likewise, the cyclobutane ring can be substituted with similar thermooxidatively stable groups. The most preferred cyclobutarene is benzocyclobutene.

The monomers of this invention are biscyclobutarene monomers. The cyclobutarene moieties of the monomer are bridged by a divalent radical that has at least one benzoxazole linkage. Processes for preparing benzoxazole linkages within the scope of this invention are described in U.S. Pat. No. 4,533,693, which is incorporated by reference herein. Preferably, the benzoxazole linkage has any one of the following formulae:

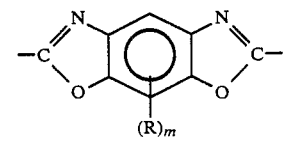

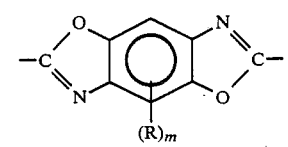

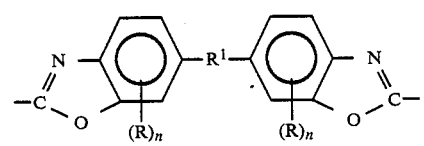

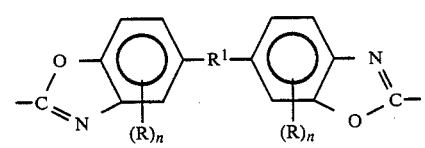

wherein
R is methyl, halo, phenyl, or phenyloxy;
$R^1$ is direct bond,

arylene, oxygen, carbonyl, sulfur, sulfinyl, or sulfonyl;
m is zero, 1 or 2; and
n is zero, 1, 2 or 3.

As the term is used herein, "arylene" refers to a divalent aromatic group. Preferred arylene is phenylene.

The most preferred benzoxazole linkage has the following formula:

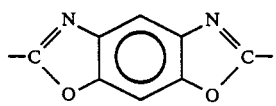

A preferred monomer with the most preferred benzoxazole linkage is a bisbenzocyclobutene monomer of the formula:

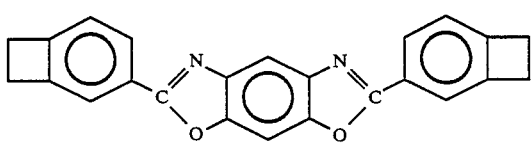

(I)

The preferred monomers can be prepared by the condensation reaction of a cyclobutarene-carboxylic acid and a diaminodihydroxyarene at elevated temperatures. A cyclobutarene-carboxylic acid is defined as a cyclobutarene substituted with carboxyl, as, for example, benzocyclobutene-4-carboxylic acid. The reaction requires a reactive reagent that acts as a dehydrating solvent for the condensation reaction and solubilizes the prepared monomer. One well known reactive reagent is polyphosphoric acid. A more preferred reagent, disclosed in Ueda et al., *J. Polymer Sci.:* Part A: Polymer Chem., 24, 1019, (1986), is a mixture of methanesulfonic acid and phosphorus pentoxide. The process conditions disclosed in Ueda for preparing polybenzoxazole polymers are generally suitable for preparing the monomers of this invention.

As an example of the monomer preparation, the monomer of formula 1 can be prepared by reacting 2 moles of benzocyclobutene-4-carboxylic acid with 1 mole of 1,3-diamino-4,6-dihydroxybenzene in the presence of a sufficient quantity of about 10 weight percent phosphorus pentoxide in methanesulfonic acid. Enough phosphorus pentoxide should be present so that the water of condensation is calculated to consume no more than 15 weight percent of the phosphorus pentoxide present at the start of the condensation reaction. The reaction mixture is stirred under nitrogen at about 100° C. for about three hours and then cooled to room temperature. The monomer can be precipitated from the mixture by contact with cold water and can be collected by filtration.

In another embodiment of this invention, reactive biscyclobutarene oligomers are prepared by reacting a cyclobutarene-carboxylic acid, a diaminodihydroxyarene, and either an aromatic diacid or an aromatic diacid chloride. The biscyclobutarene oligomers prepared by this reaction are bridged by a divalent polybenzoxazole. For purposes of describing this invention, an aromatic diacid or aromatic diacid chloride includes diacid derivatives such as aromatic dinitriles, diesters, diamides, imidate esters, and alkali and akaline earth metal salts of the diacid or diacid chloride. For example, an aromatic diester can be prepared by reacting the corresponding diacid or diacid chloride with phenol.

The required reaction conditions are similar to the conditions described for preparing the monomers of this invention. Preferred biscyclobutarene oligomers are prepared from benzocyclobutene-4-carboxylic acid and have the following formula:

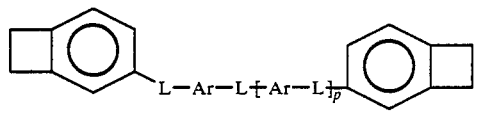

wherein L is a benzoxazole linkage of any of the formulae:

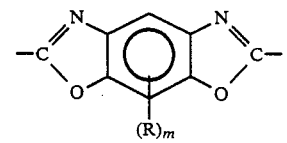

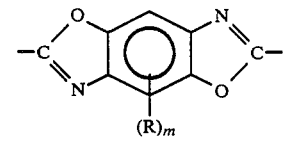

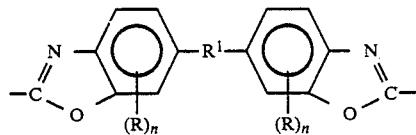

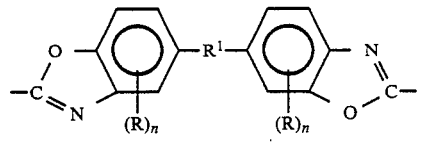

and R is methyl, halo, phenyl, or phenyloxy; $R^1$ is a direct bond,

arylene, oxygen, carbonyl, sulfur, sulfinyl, or sulfonyl;
m is zero, 1 or 2; and
n is zero, 1, 2 or 3;
Ar is arylene, biarylene, or two arylene moieties bridged by oxygen, carbonyl, sulfur, sulfinyl, or sulfonyl; and
p is either zero or an integer of 1 or more, preferably either zero or an integer between 1 and 1,000, inclusive.

Preferred arylene is phenylene; preferred oligomers are depicted when Ar in the formula is phenylene, biphenylene, and two phenylene moieties bridged by oxygen, carbonyl, sulfur, sulfinyl, or sulfonyl. The preferred benzoxazole linkage, depicted as the letter L in the formula, has the following formula:

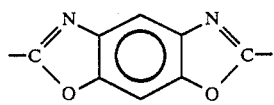

More preferred biscyclobutarene oligomers are depicted when Ar in the formula is either biphenylene or two phenylene moieties bridged by oxygen or carbonyl. The most preferred biscyclobutarene oligomer is depicted when Ar is biphenylene and the subscript n is zero, and has the following formula:

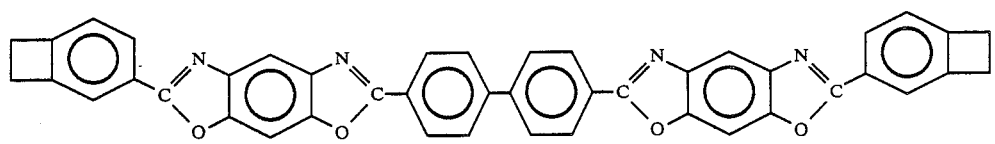

(II)

The reactive biscyclobutarene oligomers exist as a mixture of oligomers wherein the value of the subscript n for each component of the mixture varies over a wide range. The average value of the subscript n for an oligomer prepared by the method of this invention is determined by the relative proportions of cyclobutarene-carboxylic acid, diaminodihydroxyarene, and either aromatic diacid or aromatic diacid chloride employed in the reaction.

In another embodiment of this invention, two or more diaminodihydroxyarenes are reacted with a cyclobutarene-carboxylic acid and either an aromatic diacid or an aromatic diacid chloride. A reactive biscyclobutarene oligomer having an unsymmetrical divalent bridging member can thus be prepared. A biscyclobutarene having an unsymmetrical bridging member may be easier to process than a biscyclobutarene having a symmetrical bridging member (symmetry may cause crystallization which makes the melting of the monomer or oligomer more difficult). Similar results may be obtained using two or more aromatic diacids or aromatic diacid chlorides.

The biscyclobutarene monomers and reactive oligomers of this invention can be subjected to ring scission polymerization conditions to prepare highly crosslinked, three-dimensional polymeric networks that are thermoxidatively stable at high temperatures for prolonged time periods. In preferred embodiments, the prepared polymers exhibit no more than a 10 weight percent loss after exposure in air at 316° C. for 900 hours, preferably no more than a 10 weight percent loss after exposure in air at 343° C. for 200 hours. In this context, "ring scission polymerization" refers to the reaction of an opened cyclobutane ring on a cyclobutarene moiety with either another opened cyclobutane ring or a moiety capable of reacting with an opened cyclobutane ring.

When the cyclobutane ring of the cyclobutarene moiety opens, it forms a conjugated diene (orthoquinodimethane) that can react with a dienophilic moiety (a "diene loving" moiety). Typically, the opened ring reacts with another opened ring. U.S. Pat. No. 4,540,763 discloses some of the potential reactions that can occur when opened rings react with each other. Also, an opened ring can potentially react with an olefinic or acetylenic moiety via a Diels-Alder reaction as disclosed in Feiser and Feiser, *Organic Chemistry*, 3rd ed., 1980.

The cyclobutane ring of the cyclobutarene moiety can open by subjecting the monomers and reactive oligomers to sufficient heat. Typically, temperatures from about 200° C. to 300° C. are sufficient to open the ring. Polymerization solvents or catalysts are unnecessary, although a copper salt catalyst may lower the required temperature. Gamma radiation and electron beam radiation can also open the ring, but thermal radiation is preferred since it can be applied by conventional methods.

The monomers and oligomers of this invention can be copolymerized with other monomers and reactive oligomers having at least one cyclobutarene-reactive functionality. Advantageously, the comonomer or oligomer chosen will copolymerize with the monomers and oligomers of this invention to form thermooxidatively stable copolymer compositions. Preferred comonomers and oligomers are maleimides, olefins, acetylenes, cyanates, and those having at least one cyclobutarene moiety as described in U.S. Pat. No. 4,540,763 and copending U.S. application Ser. No. 835,013, filed Feb. 28, 1986. An especially preferred comonomer has the following formula:

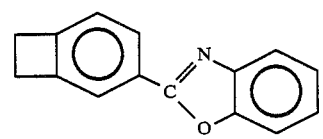

This comonomer can be prepared by reacting benzocyclobutene-4-carboxylic acid with ortho-aminophenol using reaction conditions similar to the conditions necessary for preparing the monomers of this invention described hereinbefore.

The following examples illustrate but do not limit the scope of this invention.

Example 1 Preparation of a Biscyclobutarene Oligomer With a Divalent Bridging Member Having a Benzoxazole Linkage

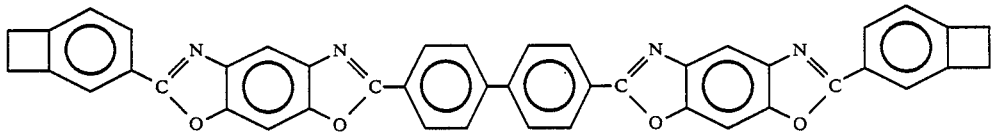

Benzocyclobutene-4-carboxylic acid ($4.70 \times 10^{-2}$ moles), 4,4'-biphenyldicarboxyl chloride ($2.35 \times 10^{-2}$ moles), 1,3-diamino-4,6-dihydroxybenzene ($4.70 \times 10^{-2}$ moles), 25.0 grams (g) phosphorus pentoxide and 225 g methanesulfonic acid are charged to a 500 milliliter (ml) resin kettle equipped with a magnetic stirring bar and a nitrogen inlet. The mixture is stirred in a nitrogen atmosphere and heated to 100° C. After 3 hours, the reaction mixture is cooled to room temperature and is poured into 1-liter of crushed ice to form a precipitate. The pH of the resulting aqueous slurry is adjusted to a pH of 9 with ammonium hydroxide. The precipitate is collected by filtration, washed thoroughly with water, and dried in a vacuum oven at 90° C. for 8 hours to give the desired product in 95 percent yield.

EXAMPLE 2

Preparation of the Polymer from the Biscyclobutarene Oligomer of Example 1 and the Termooxidative Stability of the Polymer and Other polymers A portion of the benzocyclobutene oligomer prepared from Example 1 is placed in a compression mold having a cavity shaped in the form of a disc. The mold is heated to 160° C. and sufficient pressure is applied to make the oligomer flow completely, filling the mold cavity. The mold is then heated under pressure to 270° C. over a period of 3 hours and afterwards is allowed to cool to room temperature while pressure is maintained. After cooling to room temperature, the mold is opened to reveal a solid polymer disc conforming to the shape of the mold cavity. The polymer disc is removed from the mold and is placed in a circulating air oven at 316° C. (600° F.). The disc is removed from the oven at varying times and is weighed to measure the isothermal weight loss of the polymer. After each measurement, the polymer is returned to the oven.

Another portion of the oligomer prepared from Example 1 is similarly polymerized in the compression mold and the resulting polymer is placed in the circulating air oven at 343° C. (650° F.). Again, the polymer disc is removed from the oven at varying times and is weighed to measure the isothermal weight loss.

Figure 2:
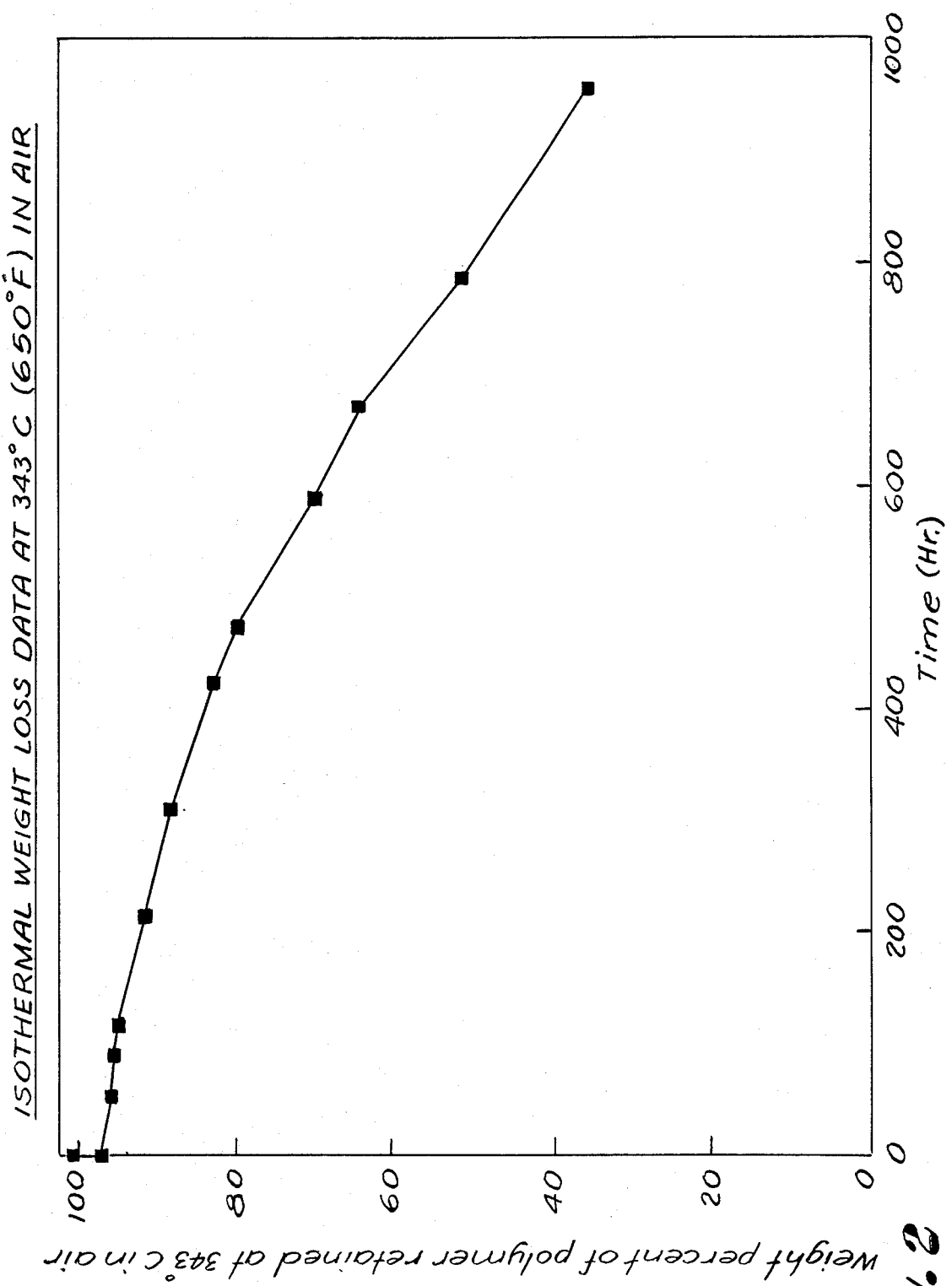

The resulting isothermal weight loss measurements at each temperature are presented in FIGS. 1 and 2.

The results at 316° C. indicate that over 90 percent of the weight of the polymer remains after exposure in air for more than 900 hours. The results at 343° C. indicate that about 90 percent of the weight of the polymer remains after exposure in air for more than 200 hours. These results indicate that a biscyclobutarene oligomer having a divalent bridging member with benzoxazole linkages exhibits outstanding thermoxidative stability at high temperatures for prolonged time periods.

The procedure of Example 1 is used to prepare a biscyclobutarene oligomer of the formula:

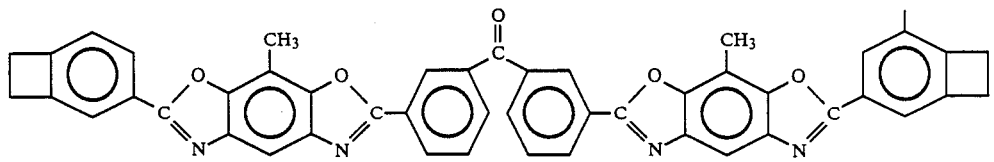

Figure 3:
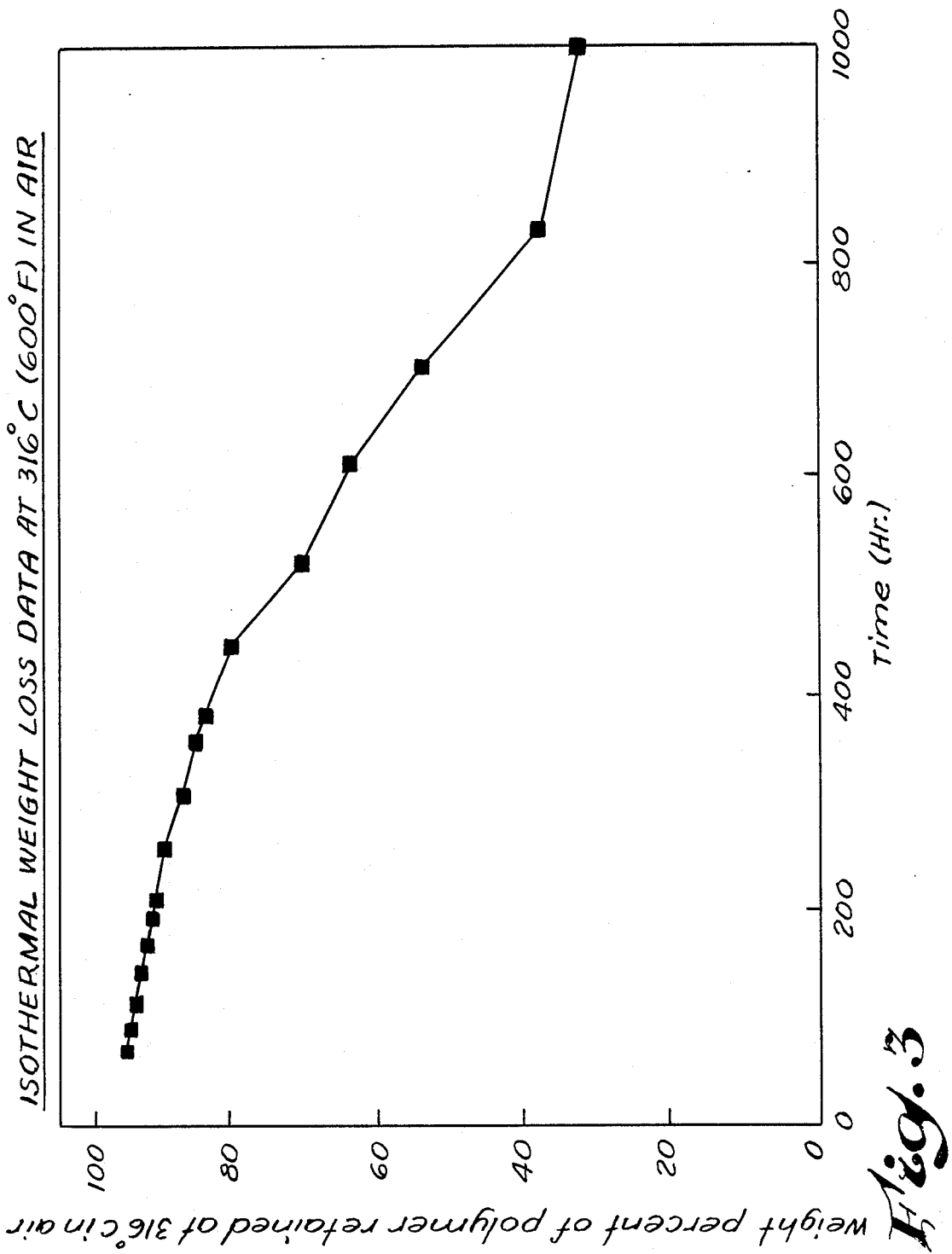
Figure 4:
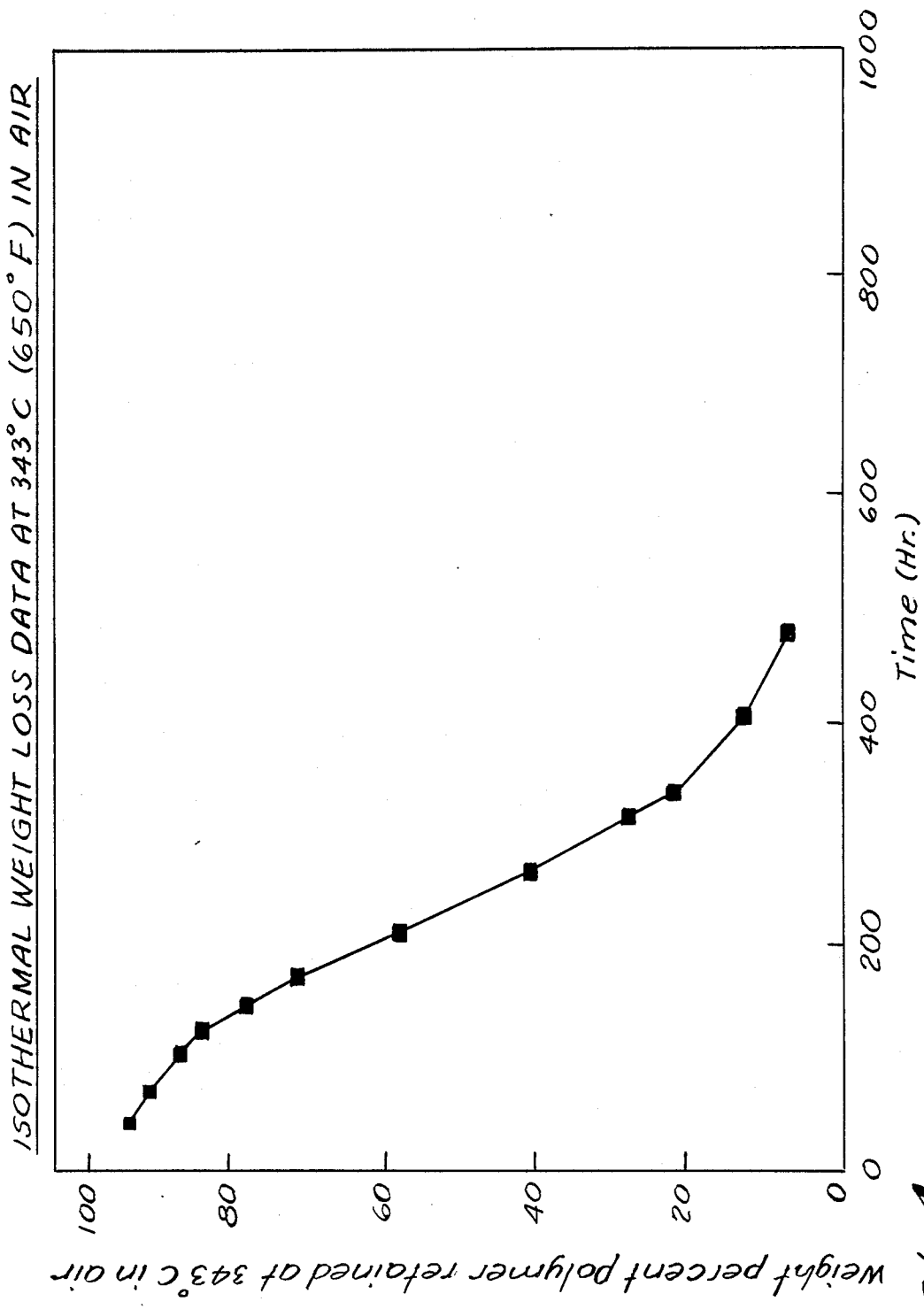

The biscyclobutarene is polymerized and analyzed for thermooxidative stability at 316° C. and 343° C. using the procedure described in this example. The resulting isothermal weight loss measurements at each temperature are presented in FIGS. 3 and 4.

Again, the results at both temperatures indicate outstanding thermooxidative stability at high temperatures for prolonged time periods.

Upon repeating the procedures of Examples 1 and 2 with other oligomers and monomers of this invention, similar outstanding results are obtained.

What is claimed is:

1. A biscyclobutarene monomer comprising two cyclobutarene moieties bridged by a divalent radical having at least one benzoxaxole linking group represented by any one of the formulae:

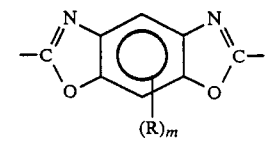

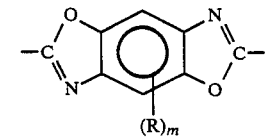

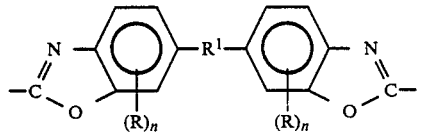

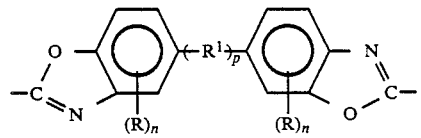

wherein
R is methyl, halo, phenyl, or phenyloxy;
R¹ is a direct bond,

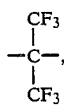

arylene, oxygen, carbonyl, sulfur, sulfinyl, or sulfonyl;
m is zero, 1 or 2; and
n is zero, 1, 2 or 3.

2. The biscyclobutarene monomer of claim 1 wherein the monomer is a bisbenzocyclobutene monomer.

3. The biscyclobutarene monomer of claim 2 wherein the benzoxazole linkage group has the formula:

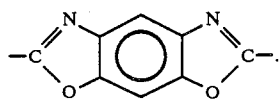

4. The biscyclobutarene monomer of claim 3 of the formula:

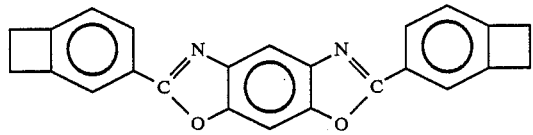

5. A biscyclobutarene oligomer comprising the reaction product of a cyclobutarene-carboxylic acid, a diaminodihydroxyarene, and either an aromatic diacid or an aromatic diacid chloride.

6. The biscyclobutarene oligomer of claim 5 wherein the cyclobutarene-carboxylic acid is benzocyclobutene-4-carboxylic acid.

7. The biscyclobutarene oligomer of claim 6 of the formula:

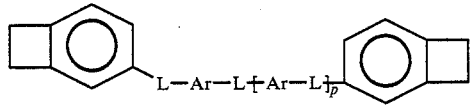

wherein L is a benzoxazole linking group of any of the formulae:

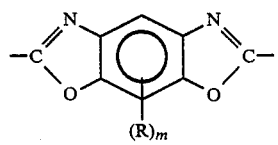

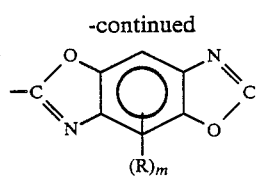

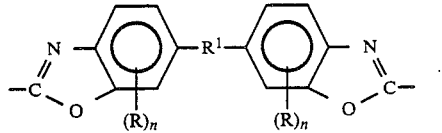

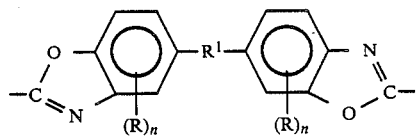

and R is methyl, halo, phenyl, or phenyloxy;
R¹ is a direct bond,

arylene, oxygen, carbonyl, sulfur, sulfinyl, or sulfonyl;
m is zero, 1 or 2; and
n is zero, 1, 2 or 3;
Ar is arylene, biarylene, or two arylene moieties bridged by oxygen, carbonyl, sulfur, sulfinyl, or sulfonyl; and
p is either zero or an integer of 1 or more.

8. The biscyclobutarene oligomer of claim 7 wherein L has the formula:

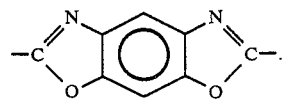

9. The biscyclobutarene oligomer of claim 8 wherein Ar is phenylene, biphenylene, or two phenylene moieties bridged by oxygen, carbonyl, sulfur, sulfinyl or sulfonyl.

10. The biscyclobutarene oligomer of claim 9 wherein Ar is biphenylene, or two phenylene moieties bridged by oxygen or carbonyl.

11. The biscyclobutarene oligomer of claim 10 wherein Ar is biphenylene.

12. The biscyclobutarene oligmer of claim 11 of the formula:

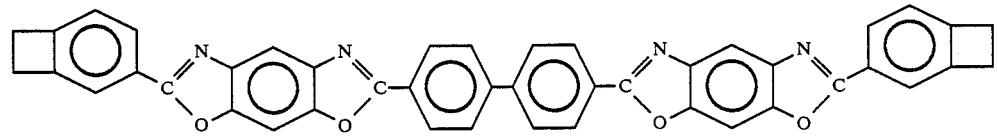

13. A process for preparing a polymer from the monomer of claim 1, comprising the step of subjecting the monomer of claim 1 to ring scission polymerization conditions.

14. A process of claim 13 wherein the polymer is a copolymer of the monomer of claim 1 and at least a second monomer or oligomer.

15. A process of claim 14 wherein the second monomer or oligomer has at least one cyclobutarene moiety.

16. A process of claim 15 wherein the second monomer or oligomer has the formula:

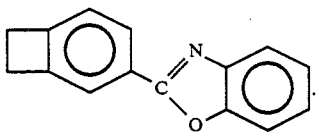

17. A process for preparing a polymer from the oligomer of claim 5, comprising the step of subjecting the oligomer of claim 5 to ring scission polymerization conditions.

18. The process of claim 17 wherein the polymer is a copolymer of the oligomer of claim 5 and at least a second oligomer or monomer.

19. The process of claim 18 wherein the second oligomer or monomer has at least one cyclobutarene moiety.

20. The process of claim 19 wherein the second monomer or oligomer has the formula:

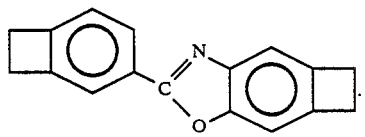

* * * * *

UNITED STATES PATENT AND TRADEMARK OFFICE
CERTIFICATE OF CORRECTION

PATENT NO. : 4,864,010   Page 1 of 10
DATED : September 5, 1989
INVENTOR(S) : Alan K. Schrock, William J. Harris, and Norman L. Madison It is certified that error appears in the above-identified patent and that said Letters Patent is hereby corrected as shown below:

Column 1, line 38, "4,540,736" should read -- 4,540,763 -- .

Column 2, the formulae should correctly read --

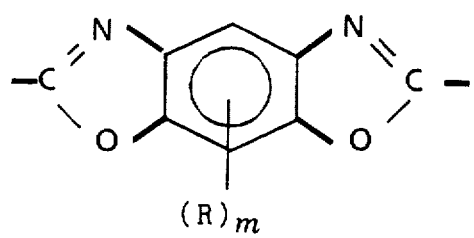

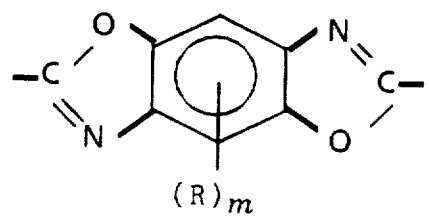

UNITED STATES PATENT AND TRADEMARK OFFICE
CERTIFICATE OF CORRECTION

PATENT NO. : 4,864,010
DATED : September 5, 1989
INVENTOR(S) : Alan K. Schrock, William J. Harris, and Norman L. Madison It is certified that error appears in the above-identified patent and that said Letters Patent is hereby corrected as shown below:

Column 2, line 55, the formulae should correctly read --

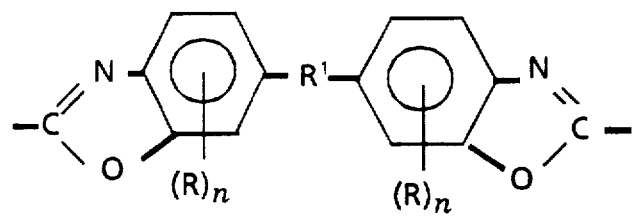

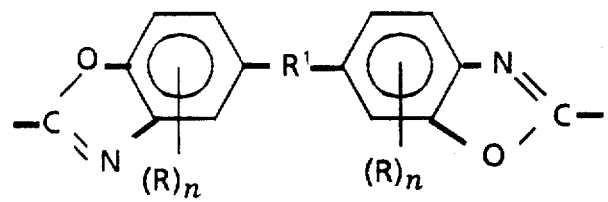

UNITED STATES PATENT AND TRADEMARK OFFICE
CERTIFICATE OF CORRECTION

PATENT NO. : 4,864,010

DATED : September 5, 1989

INVENTOR(S) : Alan K. Schrock, William J. Harris, and Norman L. Madison

It is certified that error appears in the above-identified patent and that said Letters Patent is hereby corrected as shown below:

Column 2, line 68, "is direct" should read -- is a direct --.

UNITED STATES PATENT AND TRADEMARK OFFICE
CERTIFICATE OF CORRECTION

PATENT NO. : 4,864,010

DATED : September 5, 1989

INVENTOR(S) : Alan K. Schrock, William J. Harris, and Norman L. Madison

It is certified that error appears in the above-identified patent and that said Letters Patent is hereby corrected as shown below:

Column 4, line 25, the formulae should correctly read --

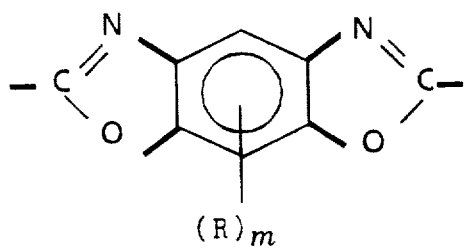

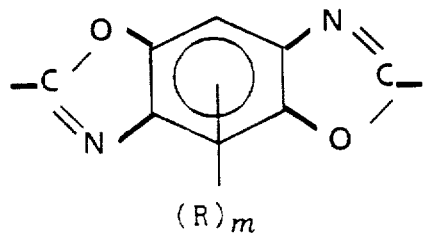

UNITED STATES PATENT AND TRADEMARK OFFICE
CERTIFICATE OF CORRECTION

PATENT NO. : 4,864,010

DATED : September 5, 1989

INVENTOR(S) : Alan K. Schrock, William J. Harris, and Norman L. Madison

It is certified that error appears in the above-identified patent and that said Letters Patent is hereby corrected as shown below:

Column 4, line 35, the formulae should correctly read --

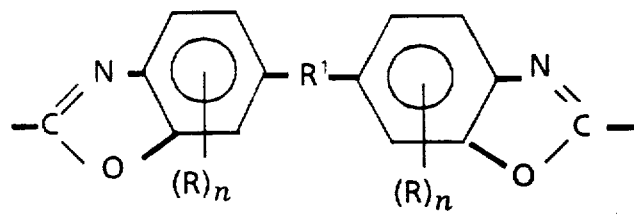

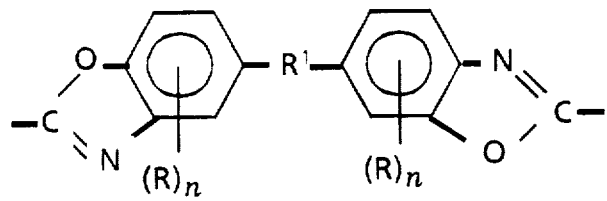

UNITED STATES PATENT AND TRADEMARK OFFICE
CERTIFICATE OF CORRECTION

PATENT NO. : 4,864.010
DATED : September 5, 1989
INVENTOR(S) : Alan K. Schrock, William J. Harris, and Norman L. Madison It is certified that error appears in the above-identified patent and that said Letters Patent is hereby corrected as shown below:

Column 7, line 39, "Termooxidative" should read -- Thermooxidative --.

Column 8, line 42, the formulae should correctly read --

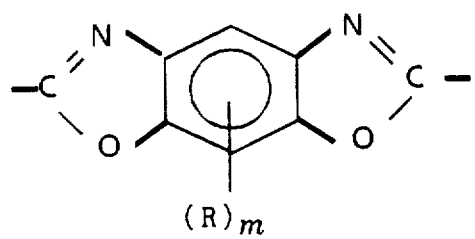

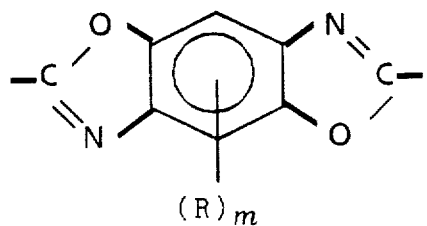

UNITED STATES PATENT AND TRADEMARK OFFICE
CERTIFICATE OF CORRECTION

PATENT NO. : 4,864,010
DATED : September 5, 1989
INVENTOR(S) : Alan K. Schrock, et al.

It is certified that error appears in the above-identified patent and that said Letters Patent is hereby corrected as shown below:

Column 8, line 57, the formulae should correctly read --

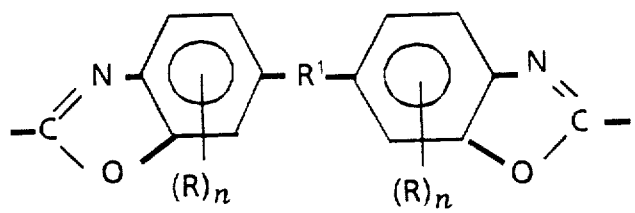

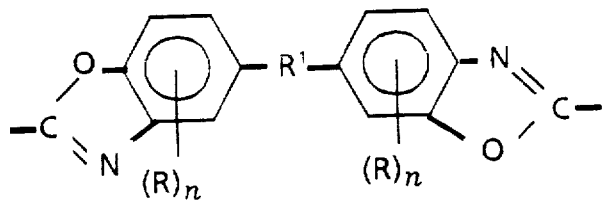

Column 9, line 3, "$R^1$ is a direct bond," should correctly read -- $R^1$ is a direct bond, or $R^1$ represents --.

UNITED STATES PATENT AND TRADEMARK OFFICE
CERTIFICATE OF CORRECTION

PATENT NO. : 4,864,010
DATED : September 5, 1989
INVENTOR(S) : Alan K. Schrock, William J. Harris, and Norman L. Madison It is certified that error appears in the above-identified patent and that said Letters Patent is hereby corrected as shown below:

Column 9, line 44, the formula should correctly read --

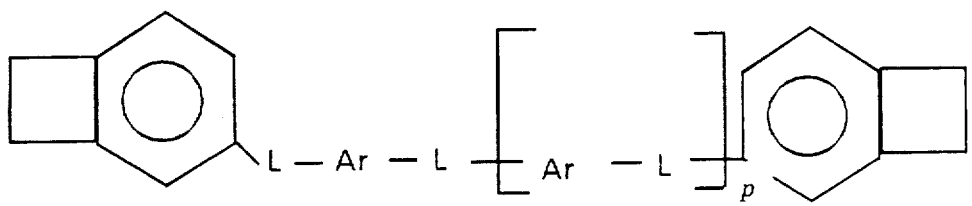

UNITED STATES PATENT AND TRADEMARK OFFICE
CERTIFICATE OF CORRECTION

PATENT NO. : 4,864,010

DATED : September 5, 1989

INVENTOR(S) : Alan K. Schrock, William J. Harris, and Norman L. Madison

It is certified that error appears in the above-identified patent and that said Letters Patent is hereby corrected as shown below:

Column 9, line 51, the formula should correctly read --

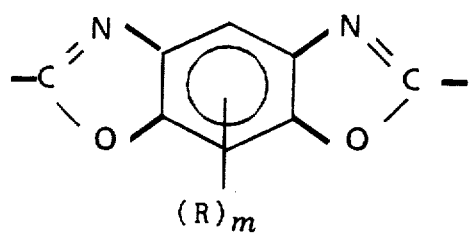

Column 10, line 1, the formula should correctly read --

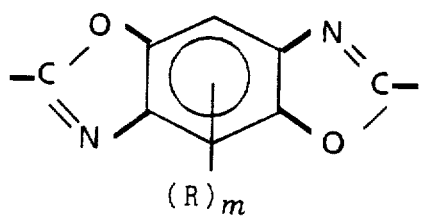

UNITED STATES PATENT AND TRADEMARK OFFICE
CERTIFICATE OF CORRECTION

PATENT NO. : 4,864,010
DATED : September 5, 1989
INVENTOR(S) : Alan K. Schrock, William J. Harris, and Norman L. Madison It is certified that error appears in the above-identified patent and that said Letters Patent is hereby corrected as shown below:

Column 10, line 9, the formulae should correctly read --

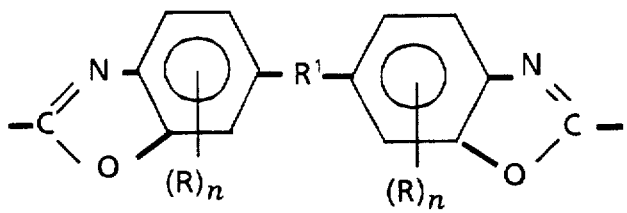

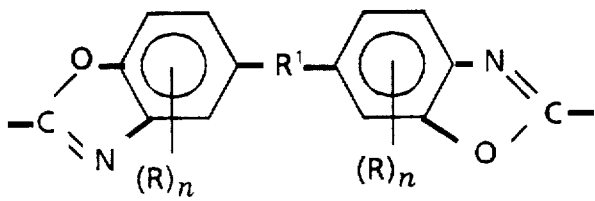

Column 11, line 1, "A process" should read -- The process --.

Column 11, line 4, "A" should read --The -- .

Signed and Sealed this

Thirteenth Day of October, 1992

Attest:

DOUGLAS B. COMER

Attesting Officer

Acting Commissioner of Patents and Trademarks